(12) United States Patent
Cha et al.

(10) Patent No.: US 10,324,049 B2
(45) Date of Patent: Jun. 18, 2019

(54) ROCK SAMPLE PREPARATION METHOD BY USING FOCUSED ION BEAM FOR MINIMIZING CURTAIN EFFECT

(71) Applicant: Saudi Arabian Oil Company, Dhahran (SA)

(72) Inventors: Dong kyu Cha, Dhahran (SA); Sultan Enezi, Dhahran (SA); Mohammed Al Otaibi, Dhahran (SA); Ali Abdallah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/685,732

(22) Filed: Aug. 24, 2017

(65) Prior Publication Data

US 2018/0231477 A1 Aug. 16, 2018

Related U.S. Application Data

(60) Provisional application No. 62/459,391, filed on Feb. 15, 2017.

(51) Int. Cl.
*G01N 23/04* (2018.01)
*G01N 23/046* (2018.01)
(Continued)

(52) U.S. Cl.
CPC ............ *G01N 23/046* (2013.01); *G01N 1/28* (2013.01); *G01N 23/225* (2013.01); *G01N 33/24* (2013.01);
(Continued)

(58) Field of Classification Search
CPC .... G01N 23/046; G01N 33/24; H01J 37/1478
See application file for complete search history.

(56) References Cited

U.S. PATENT DOCUMENTS 5,798,529 A * 8/1998 Wagner ................. G01B 15/00
250/492.21
6,646,259 B2 11/2003 Chang et al.
(Continued)

FOREIGN PATENT DOCUMENTS

CN 104198766 A 12/2014
WO WO2014106200 A1 7/2014

OTHER PUBLICATIONS

Elgmati et al: . "Submicron-Pore Characterization of Shale Gas Plays", SPE 144050 North American Unconventional Gas Conference and Exhibition, The Woodlands, Texas, USA, Jun. 14-16, 2011 pp. 1-19.
(Continued)

*Primary Examiner* — Hugh Maupin
(74) *Attorney, Agent, or Firm* — Bracewell LLP; Constance G. Rhebergen; Brian H. Tompkins

(57) ABSTRACT

A process for the preparation and imaging of a sample of rock from an oil and gas reservoir is provided. A sample of reservoir rock may be obtained, such as from a core sample obtained using a core sampling tool inserted in a wellbore extending into an oil and gas reservoir. A photoresist may be deposited on the surface of reservoir rock sample to form a homogenous layer. The photoresist-coated surface of the reservoir rock sample may be imaged using a focused ion beam (FIB). The photoresist protects the pores and other surface features of the rock from damage or implantation by the FIB ion beam and thus minimizes the curtain effect in the resulting images.

16 Claims, 4 Drawing Sheets

(51) Int. Cl.
*G01N 33/24* (2006.01)
*H01J 37/147* (2006.01)
*G01N 23/225* (2018.01)
*G01N 1/28* (2006.01)

(52) U.S. Cl.
CPC ..... *H01J 37/1478* (2013.01); *H01J 2237/049* (2013.01); *H01J 2237/21* (2013.01); *H01J 2237/31749* (2013.01)

(56) References Cited

U.S. PATENT DOCUMENTS

| | | | |
|---|---|---|---|
| 8,163,145 | B2 | 4/2012 | Nadeau et al. |
| 8,822,921 | B2 | 9/2014 | Schmidt et al. |
| 8,859,963 | B2 | 10/2014 | Moriarty et al. |
| 8,912,490 | B2 | 12/2014 | Kelley et al. |
| 9,047,513 | B2 | 6/2015 | Derzhi et al. |
| 9,064,328 | B2 | 6/2015 | Carpio et al. |
| 9,111,720 | B2 | 8/2015 | Kelley et al. |
| 9,127,529 | B2 | 9/2015 | Guzman et al. |
| 9,279,752 | B2 | 3/2016 | Moriarty et al. |
| 9,412,560 | B2 | 8/2016 | Stone et al. |
| 9,488,554 | B2 | 11/2016 | Schmidt et al. |
| 2010/0142259 | A1* | 6/2010 | Drndic .................. B82Y 10/00 365/158 |
| 2013/0259190 | A1* | 10/2013 | Walls ..................... G01N 23/22 378/9 |
| 2015/0000903 | A1* | 1/2015 | Ly ...................... G06K 9/00127 166/250.02 |
| 2015/0041667 | A1* | 2/2015 | Bhattacharjee ....... H01J 37/244 250/394 |
| 2015/0330877 | A1 | 11/2015 | Schmidt et al. |
| 2016/0093094 | A1 | 3/2016 | Walls et al. |
| 2017/0065974 | A1* | 3/2017 | Bollstrom .............. D21H 19/38 |
| 2017/0108483 | A1* | 4/2017 | Clark .................... G01N 15/08 |

OTHER PUBLICATIONS

International Search Report and Written Opinion for International Application No. PCT/US2018/018341; International Filing Date Feb. 15, 2018; Report dated May 30, 2018 (pp. 1-14).
Lemmens et al: "FIB/SEM and SEM/EDX: a New Dawn for the SEM in the Core Lab?", Petrophysics, vol. 52 No. 6 Dec. 1, 2011 (Dec. 1, 2011), pp. 452-456.
Tomutsa et al: "Focussed Ion Beam Assisted Three-Dimensional Rock Imaging at Submicron Scale" Lawrence Berkeley National Laboratory, May 9, 2003, XP055476657, Retrieved from the Internet: https://escholarship.org/uc/item/4045j24n.

* cited by examiner

ROCK SAMPLE PREPARATION METHOD BY USING FOCUSED ION BEAM FOR MINIMIZING CURTAIN EFFECT

CROSS-REFERENCE TO RELATED APPLICATIONS

This application claims priority from U.S. Provisional Application No. 62/459,391 filed Feb. 15, 2017, and titled "ROCK SAMPLE PREPARATION METHOD BY USING FOCUSED ION BEAM FOR MINIMIZING CURTAIN EFFECT." For purposes of United States patent practice, this application incorporates the contents of the Provisional Application by reference in its entirety.

BACKGROUND

Field of the Disclosure

The present disclosure generally relates to oil and gas drilling. More specifically, embodiments of the disclosure relate to the analysis of rock from an oil and gas reservoir.

Description of the Related Art

Wells may be drilled into rocks to access fluids stored in geographic formations having hydrocarbons. These geographic formations may be referred to as a "reservoirs." A variety of techniques exist for determining the presence and amount of hydrocarbons in such reservoirs. In some instances, a sample of rock and fluids may be collected downhole in the wellbore of the well and retrieved to the surface for further analysis. The sample may be analyzed to quantify the amount and value of hydrocarbons (for example, oil and gas) in the reservoir and obtain other information about the reservoir. The analysis of a core sample may also determine the rate at which the identified oil and gas may be produced and aid in identifying techniques for extracting the oil and gas and maximizing recovery from the reservoir.

However, analyzing a sample from a reservoir may be challenging and may impact subsequent quantification of hydrocarbons in the reservoir. The analysis of a sample may include various imaging techniques that are susceptible to different artifacts and other effects that impact the accuracy of the generated image of the rock. For example, the heterogeneity and surface roughness of a rock sample may affect the resulting image produced during image processing and three-dimensional (3D) reconstruction of the rock sample.

SUMMARY

One technique used to analyze rock samples from a reservoir is focused ion beam (FIB). FIB systems may be used to generate images for subsequent analysis of the properties of rock samples, such as samples of rock from an oil and gas reservoir (referred to as "reservoir rock samples"). Such properties may include, for example, permeability, porosity, and wettability. However, the surface features and porosity of a rock sample may cause an imaging artifact referred to as "curtain effect" (also referred to as "curtaining effect") on the ion-milled cross-sectional area. For example, FIG. 1 is a schematic diagram of the curtain effect that may be caused during imaging of a reservoir rock sample 100 according to prior art techniques. FIG. 1 depicts an FIB process performed on a reservoir rock sample 100, such as to generate images for analysis of the sample 100. The reservoir rock sample 100 may include various surface features 102, such as pores, cracks, and the like. After application of an FIB 104, damage and implantation from the FIB 104 may produce a curtain effect (shown by dashed lines 106) as artifacts in the resulting images produced via the FIB 104. This curtain effect may impact subsequent analysis of the resulting images and determination of rock properties such as porosity and permeability.

In one embodiment, a method of imaging a sample of rock from an oil and gas reservoir is provided. The method includes depositing a photoresist on a surface of the rock sample and subjecting the photoresist-coated surface of the rock sample to a focused ion beam (FIB) to generate a digital image of the rock sample. In some embodiments, the method includes preparing the rock sample from a core sample obtained from a wellbore extending into the oil and gas reservoir. In some embodiments, the method includes removing the photoresist from the photoresist-coated surface of the rock sample. In some embodiments, removing the photoresist includes exposing the rock sample having the photoresist to an electron beam. In some embodiments, the FIB is a gallium ion beam. In some embodiments, subjecting the photoresist-coated surface of the rock sample to a focused ion beam (FIB) includes milling a layer of the photoresist-coated surface of the rock sample via the focused ion beam. In some embodiments, depositing the photoresist on a surface of the rock sample includes spin coating the photoresist on the surface of the rock sample. In some embodiments, the FIB system is a focused ion beam-scanning electron microscopy (FIB-SEM) system. In some embodiments, the digital image is a two-dimensional (2D) image or a three-dimensional (3D) image. In some embodiments, the digital image is a three-dimensional (3D) digital image generated from two or more two-dimensional (2D) digital images of the rock sample. In some embodiments, the photoresist is SU-8 photoresist. In some embodiments, the method includes curing the photoresist at a temperature after depositing the photoresist.

In another embodiment, a system is provided that includes means for coating a surface of a rock sample, the rock sample having a photoresist deposited on the surface, and a focused ion beam (FIB) system configured to receive the rock sample having the photoresist and generate a digital image of the rock sample. In some embodiments, the FIB system includes a gallium ion beam. In some embodiments, the FIB system is a focused ion beam-scanning electron microscopy (FIB-SEM) system. In some embodiments, the photoresist is SU-8 photoresist.

In another embodiment, a method of analyzing rock from an oil and gas reservoir is provided. The method includes obtaining a rock sample having a photoresist deposited on the surface, and generating a digital image of a rock sample having a photoresist, such that the digital image is generating using a focused ion beam (FIB). The method further includes analyzing the digital image to determine a property of the rock sample. In some embodiments, the digital image is a three-dimensional (3D) image, and analyzing the digital image to determine a property of the rock sample includes analyzing the digital image to determine a porosity of the rock sample. In some embodiments, the method includes depositing a layer of a photoresist on a surface of the rock sample. In some embodiments, the photoresist is SU-8 photoresist.

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure include the preparation and imaging of a sample of reservoir rock by depositing a photoresist on the surface of the sample before imaging using FIB. A sample of reservoir rock may be obtained, such as from a core sample acquired via a core sampling tool inserted in a wellbore extending into an oil and gas reservoir. A photoresist (for example, a liquid photoresist) may be deposited on the surface of reservoir rock sample to form a layer that fills pores and other features of the surface of the reservoir rock sample. The photoresist-coated surface of the reservoir rock sample may be imaged using an FIB process. The photoresist protects the pores and other surface features of the rock from damage or implantation by the FIB and thus minimizes any resulting curtain effect in the images generated via the FIB process.

Advantageously, the application of the photoresist to a rock sample does not require substantial new equipment, such as a flip stage, for imaging reservoir rock samples, and may be more cost-effective than purchasing additional equipment or tools. Moreover, the photoresist may fill and protect the inner surfaces of pores and other surface features that other techniques, such as solid metal deposition (for example, platinum deposition), are unable to protect.

Figure 1:
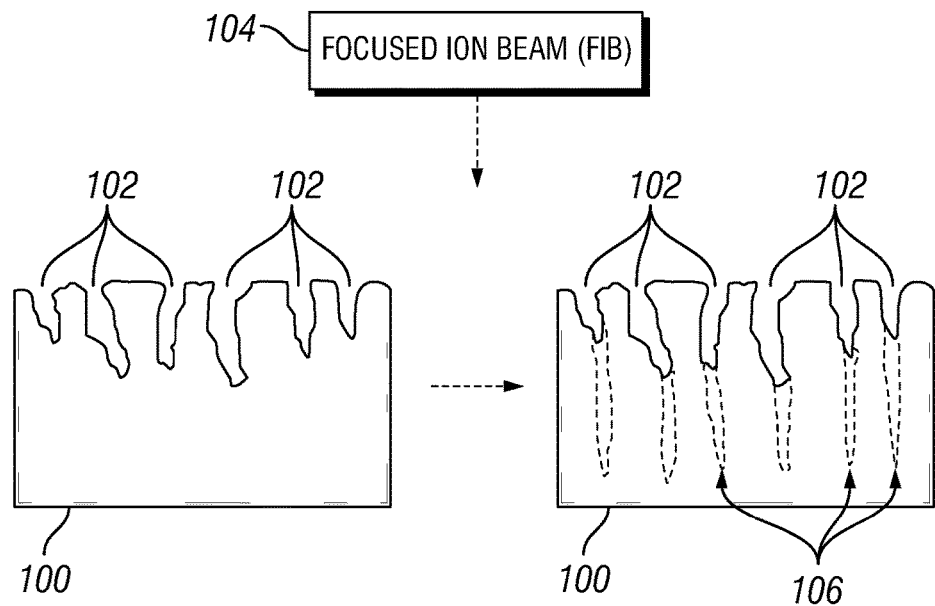
FIG. 1 is a schematic diagram of a prior art FIB process performed on a reservoir rock sample.
Figure 2A:
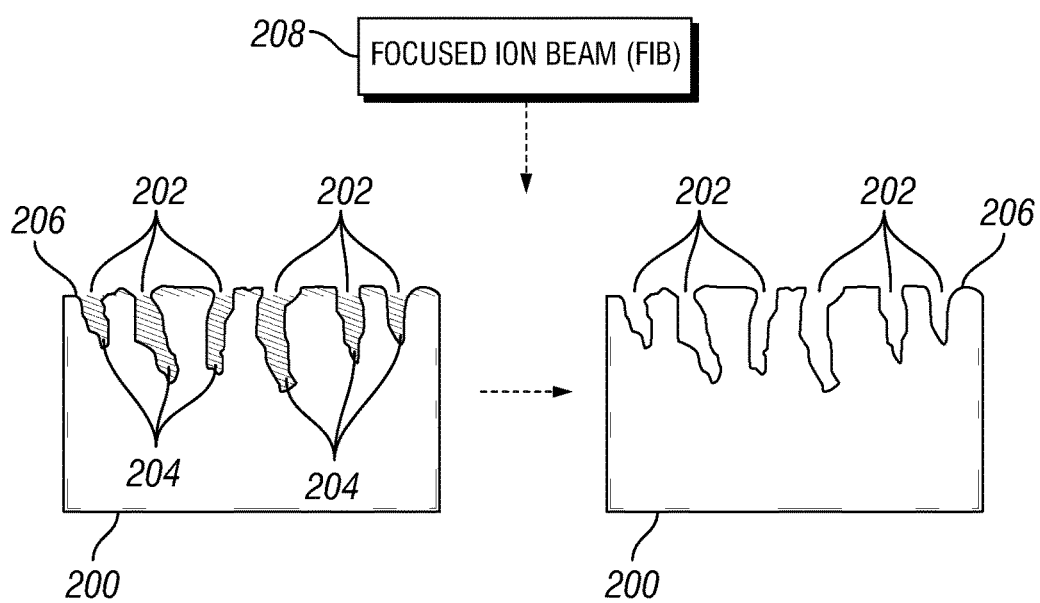
FIG. 2A is a schematic diagram of an FIB process performed on a reservoir rock sample with a photoresist in accordance with an embodiment of the disclosure.

FIG. 2A depicts an FIB process performed on a sample of reservoir rock 200 having a photoresist to minimize a curtain effect produced by ion damage or implantation from an FIB. As shown in FIG. 2A, the reservoir rock sample 200 may include various surface features 202, such as pores, voids, cracks, and the like. A liquid photoresist 204 may be deposited on a surface 206 of the rock sample 200, such as by spin coating the photoresist onto the surface 206. As shown in FIG. 2A, the photoresist 204 may fill the various surface features 202 and protect the surface 206 from an FIB 208. As also shown in FIG. 2A, the photoresist 204 may be deposited in a layer having a non-uniform thickness along the surface 206 of the rocks sample 200. The photoresist 204 may also deposit in the inner surfaces of pores and other features of the rock sample 200 to further protect the inner surfaces and aid in minimizing any curtain effect. As also shown in FIG. 2A, any curtain effect in images produced by the FIB 208 is minimized as compared to images produced on rock samples that do not have a photoresist on the surface (shown in FIG. 1). The filled photoresist 204 may be subsequently removed by exposing the rock sample 200 to an electron beam. For example, as discussed in the disclosure, the photoresist 204 may be removed using an electron microscope (such as a transmission electron microscope (TEM) or scanning electron microscope (SEM)) adapted for removal of the photoresist.

Figure 2B:
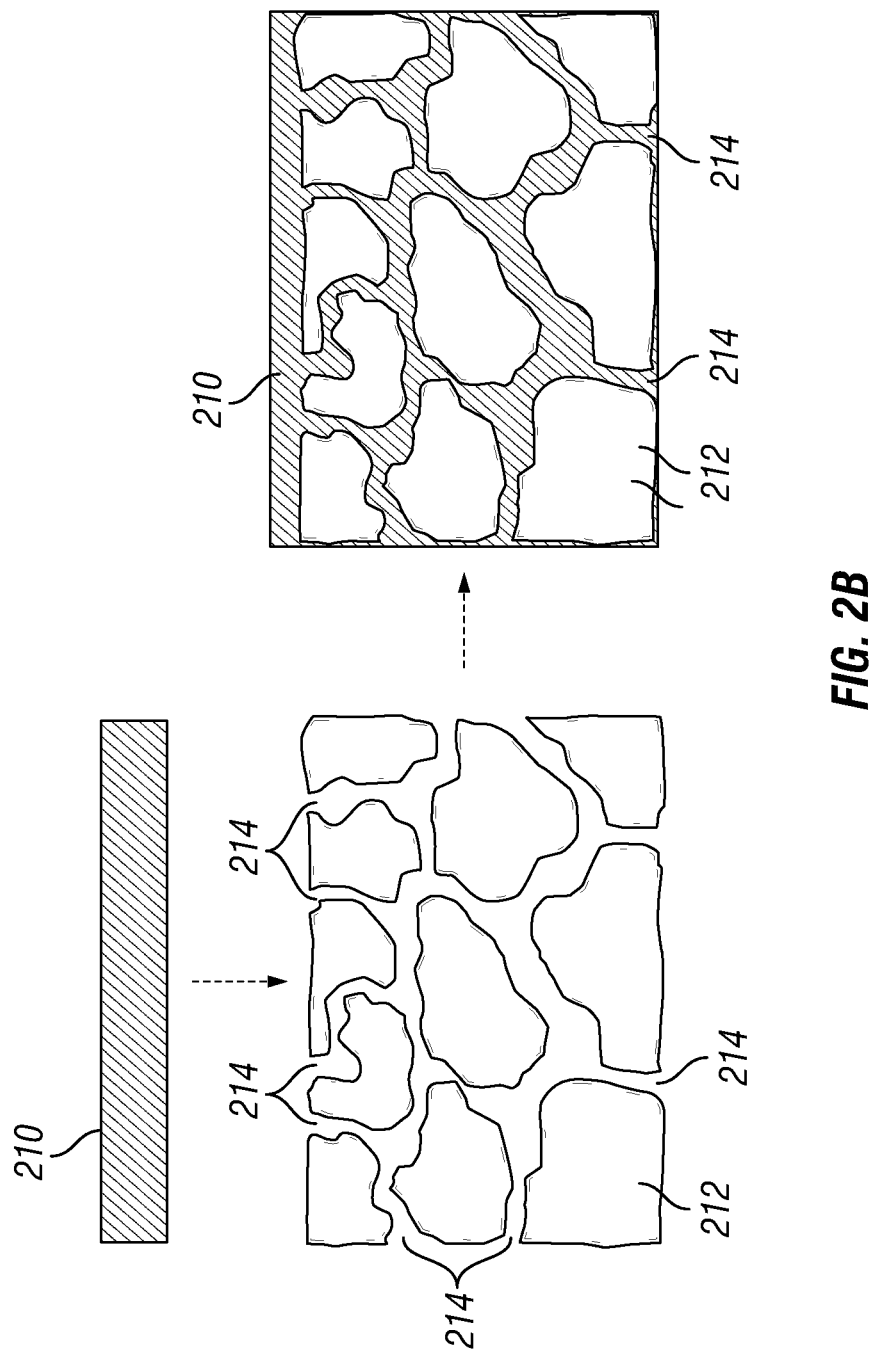
FIG. 2B is a schematic diagram of the application of photoresist to a reservoir rock sample in accordance with an embodiment of the disclosure.

Further, it should be appreciated that a reservoir rock sample has a relatively high porosity and connectivity as compared to other objects imaged by an FIB process. Consequently, a liquid photoresist applied (for example, via spin coating, injection, or both) to a reservoir rock sample may fill-up and occupy voids, pores, and other surface features of a reservoir rock sample. FIG. 2B depicts an example application of a liquid photoresist 210 to a reservoir rock sample 212. As shown in FIG. 2B, the reservoir rocks sample 212 includes connected spaces 214 (for example, pores and voids). As shown in FIG. 2B, the applied photoresist 210 may fill the connected spaces 214 to protect the inner surfaces of the spaces and aid in minimizing any curtain effect.

Figure 3:
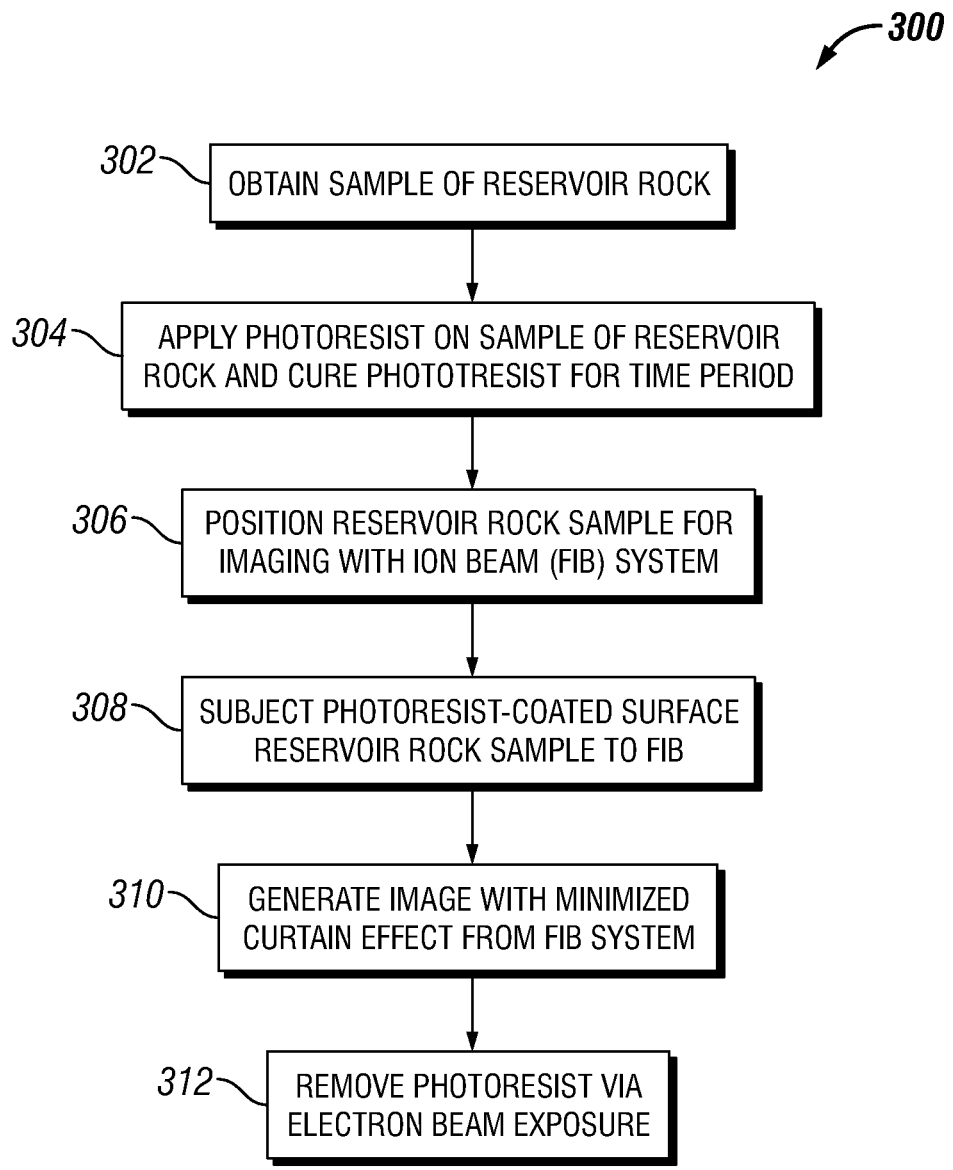
FIG. 3 is a block diagram of a process for preparation and imaging of a sample of reservoir rock in accordance with an embodiment of the disclosure.

FIG. 3 depicts a process 300 for preparation and imaging of a sample of reservoir rock in accordance with an embodiment of the disclosure. Initially, a sample of reservoir rock may be obtained (block 302). For example, in some embodiments a core sample may be obtained from a wellbore extending into an oil and gas reservoir. Such core samples may be obtained using a core sampling tool inserted into the wellbore that acquires the core sample and provides for retrieval of the core sample to the surface. In some embodiments, a core sample may be cut, sliced, or otherwise processed to prepare a sample of reservoir rock. For example, in some embodiments multiple slices of a core sample may be prepared and imaged according to the process 300 illustrated in FIG. 3.

Next, a photoresist may be deposited on the surface of the reservoir rock sample and, in some embodiments, the deposited photoresist may be cured for a time period (block 304). In some embodiments, the deposited photoresist may be cure for a time period of about 1 minute to about 5 minutes at room temperature, depending on the thickness of the deposited photoresist. In other embodiments, the deposited photoresist may not be cured before continuing with the process 300. In some embodiments, the photoresist may be deposited on the reservoir rock sample via spin coating. In some embodiments, the photoresist may be injected into the reservoir rock sample. In some embodiments, the photoresist may be applied to the reservoir rock by a combination of spin coating and injection. For example, the injection may include applying the photoresist to the reservoir rock sample under a vacuum for a time period, such as about 24 hours. In some embodiments, spin coating may be performed after the injection of photoresist, resulting in the removal of excess photoresist. In other embodiments, the photoresist may be deposited on the reservoir rock sample using other techniques. In some embodiments, the photoresist is an epoxy-based liquid photoresist. In some embodiments, the photoresist is SU-8 photoresist. In some embodiments, the SU-8 photoresist may be SU-8 2000 photoresist manufactured by MicroChem Corp. of Westborough, Mass., USA. In some embodiments, other suitable photoresists may be used. For example, in other embodiments, the deposited photoresist may be poly(methyl methacrylate) (PMMA) or poly(methyl glutarimide) (PMGI).

The photoresist-coated surface of the reservoir rock sample may then be positioned for imaging with an FIB system (block 306) and subjected to an FIB (block 308). One or more digital images of the reservoir rock sample may be generated using the FIB system (block 308). As discussed supra, the photoresist may protect pores, voids, and other surface features of the reservoir rock sample from the ion beam of the FIB system, thus minimizing a curtain effect in the generated digital images. In some embodiments, the digital images may be two-dimensional (2D) images or three-dimensional (3D) images. In some embodiments, a three-dimensional (3D) image may be generated from multiple two-dimensional (2D) images. For example, in some embodiments, an FIB system may be used to create multiple two-dimensional (2D) sections of the rock sample to subsequently generate a three-dimensional (3D) image that models the pores and other features of the rock sample. In such embodiments, for example, the digital images may be generated using a dual beam FIB-SEM system. In these embodiments, a digital image of the rock sample having the photoresist may be generated using the SEM beam, after which a layer of the rock sample may be removed via milling by the FIB, another digital image of the rock sample may be generated using SEM, and so on. In this manner, multiple two-dimensional (2D) images of the rock sample may be generated and used to subsequently generate a three-dimensional (3D) image of the rock sample.

As will be appreciated, the FIB system and generated images may be used to determine properties of the rock such as permeability, porosity, and wettability using techniques known in the art, such as digital rock physics (DRP). The minimized curtain effect may improve the accuracy of the generated images and the subsequent determinations of properties of the rock. For example, a generated digital image using the techniques described in the disclosure may enable improved identification of voxels in a three-dimensional (3D) image as mineral, organic matter, or pore, thus improving the quantification of mineral, organic matter, or pores in the rock sample and the subsequent determination of properties such as porosity and permeability.

In some embodiments, the photoresist may be removed from the reservoir rock sample by exposing the reservoir rock sample to an electron beam (block 310). The removal of the photoresist may enable the use of the reservoir rock sample in other processes. In some embodiments, the photoresist may be removed by exposure to an electron beam or ion beam the FIB system (for example, an electron beam provided by an FIB-SEM system). In some embodiments, the photoresist may be removed using an electron microscope (such as a transmission electron microscope (TEM) or scanning electron microscope (SEM)) adapted for removal of the photoresist. After removal of the photoresist, the reservoir rock sample may be analyzed using other analysis or imaging techniques.

Figure 4:
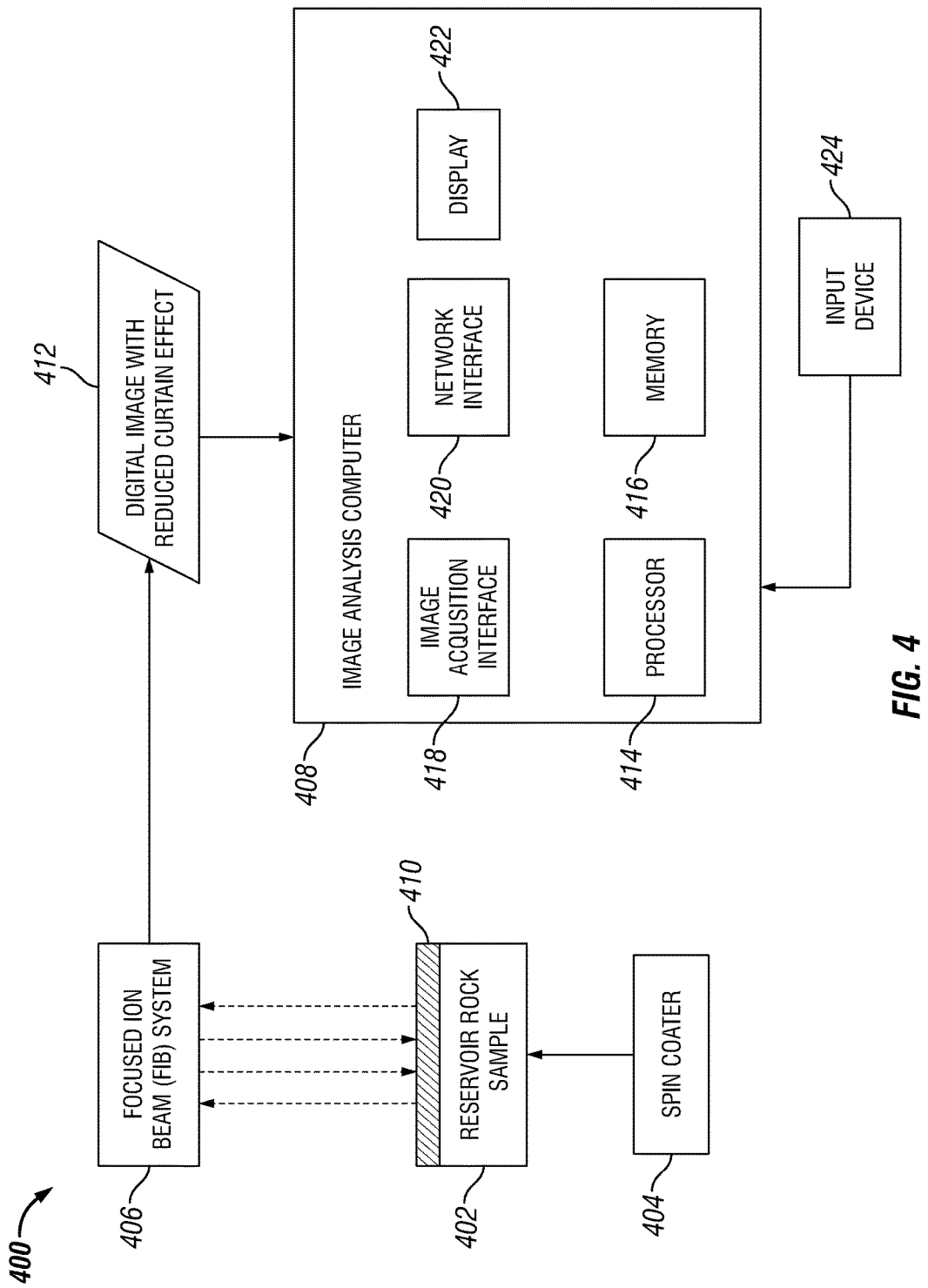
FIG. 4 is a block diagram of a system for preparation and imaging of a sample of reservoir rock in accordance with an embodiment of the disclosure.

FIG. 4 is a block diagram of a system 400 for imaging a reservoir rock sample 402 in accordance with an embodiment of the disclosure. As shown in FIG. 4, the system 400 may include a spin coater 404, a focused ion beam system 406, and an image analysis computer 408. In some embodiments, the focused ion beam system 406 and an image analysis computer 408 may be separate components, as shown in FIG. 4. In other embodiments, the focused ion beam system 406 and the image analysis computer 408 may be a single component, such that the focused ion beam system 406 includes a computer for analyzing images generated by the FIB process.

As described in the disclosure, the spin coater 404 may deposit a photoresist 410 on the surface of a reservoir rock sample 402 to prepare the reservoir rock sample 402 for imaging. As will be appreciated, the reservoir rock sample 402 may be placed in the spin coater 404, and the photoresist may be deposited until a layer is formed on the surface of the reservoir rock sample 402. In some embodiments, the layer may be a generally homogenous layer on the surface of the reservoir rock sample 402.

In some embodiments, the photoresist 410 may be injected into the reservoir rock sample 402 to prepare the reservoir rock sample 402 for imaging. The injection may include applying the photoresist 410 to the reservoir rock sample 402 under a vacuum for a time period, such as about 24 hours. In some embodiments, the spin coater 404 may be used after injection, resulting in the removal of excess photoresist.

The FIB system 406 may perform an FIB process on the reservoir rock sample 402 with the photoresist 410, such as to obtain digital images of the reservoir rock sample 402 for subsequent determination of properties of the reservoir rock. In some embodiments, the FIB system 406 uses a gallium (Ga) ion source. In other embodiments, other ion sources may be used. In some embodiments, the FIB system 406 may be primarily capable of imaging of an object and, at higher beam currents, milling or sputtering an object surface. As will be appreciated, such sputtering or milling may also occur at lower beam currents during an imaging process. In some embodiments, the resolution of the FIB system 406 may be in the range of 5 nanometers (nm) to about 10 nm. In some embodiments, the FIB system 406 may perform an initial ion beam milling at an accelerating voltage of about 30 kilovolts (kV) and a beam current of about 3 nanoamperes (nA) to about 5 nA. In such embodiments, the duration may be determined based on milling area and depth. After the initial ion beam milling, the FIB system 406 may perform a cleaning cross-section milling at an accelerating voltage of about 2 kV to about 5 kV and a beam current of about 2 picoamperes (pA) to about 10 pA.

In some embodiments, the system 400 may include a focused ion beam scanning electron microscope (FIB-SEM) system. As will be appreciated, an FIB-SEM system includes an ion beam column and an electron beam column. In such embodiments, the FIB-SEM system may be used to generate a digital image of the rock sample having the photoresist using SEM, remove a layer of the rock sample via milling by the FIB, generate another digital image of the rock sample using SEM, remove a layer of the rock sample via milling by the FIB, and so on. In this manner, multiple two-dimensional (2D) images of the rock sample may be generated and used to subsequently generate a three-dimensional (3D) image of the rock sample. In some embodiments, the FIB system 406 may be used with energy-dispersive X-ray spectroscopy (EDS) or may include such capability.

The FIB system 406 may generate one or more digital images 412 with a minimized curtain effect. In some embodiments, the one or more digital images 412 may be used to reconstruct a 3D image of the reservoir rock sample 402. For example, in some embodiments the digital images 412 generated by the FIB system 406 may include a stack of sliced images with a minimized curtain effect. The stack of sliced images may be used to generate a three-dimensional (3D) digital image of the reservoir rock sample 402.

The image analysis computer 408 may acquire images generated by the FIB system 406. The image analysis computer 408 may include, for example, a processor 414, a memory 416, an image acquisition interface 418, and a display 422. In some embodiments, the image analysis computer 408 may also include a network interface 420. In some embodiments, image analysis computer 408 may include a personal computer, such as a desktop computer, a laptop computer, a tablet computer, or the like.

The processor 414 (as used the disclosure, the term "processor" encompasses microprocessors) may include one or more processors having the capability to receive and process images generated by the FIB system 406. In some embodiments, the processor 414 may include an application-specific integrated circuit (AISC). In some embodiments, the data acquisition processor 414 may include a reduced instruction set (RISC) processor. Additionally, the processor 414 may include single-core processors and multicore processors, and may include graphics processors. The processor 414 may receive instructions and data from memory 416.

The memory 416 (which may include one or more tangible non-transitory computer readable storage mediums) may include volatile memory, such as random access memory (RAM), and non-volatile memory, such as ROM, flash memory, a hard drive, any other suitable optical, magnetic, or solid-state storage medium, or a combination thereof. The memory 416 may be accessible by the processor 414 and may store executable computer code. For example, the executable computer code may include instructions executable by a processor (for example, the processor 414) to acquire, analyze, and display images generated by the FIB system 406. In some embodiments, the instructions may include instructions for the determination of porosity, permeability, or both from three-dimensional (3D) digital images produced using the techniques described.

The image acquisition interface 418 may provide for communication between the image analysis computer 408 and the FIB system 406. The image acquisition interface 418 may include a wired interface or a wireless interface and may provide for communication over wired networks or wireless networks. For example, the image acquisition interface 418 may receive digital image data from the FIB system 418 for processing and display by the image analysis computer 408.

The network interface 420 may provide for communication between the image analysis computer 406 and other devices. The network interface 420 may include a wired network interface card (NIC), a wireless (for example, radio frequency) network interface card, or combination thereof. The network interface 420 may include circuitry for receiving and sending signals to and from communications networks, such as an antenna system, an RF transceiver, an amplifier, a tuner, an oscillator, a digital signal processor, and so forth. The network interface 420 may communicate with networks such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (for example, IEEE 802.11 standards), and other standards, protocols, and technologies. In some embodiments, the network interface 420 may enable communication over industrial control networks.

The display 422 may include a cathode ray tube (CRT) display, liquid crystal display (LCD), an organic light emitting diode (OLED) display, or other suitable display. The display 422 may display a user interface (for example, a graphical user interface) that may display images acquired from the FIB system 406. In accordance with some embodiments, the display 422 may be a touch screen and may include or be provided with touch sensitive elements through which a user may interact with the user interface. In some embodiments, the user interface may provide for viewing and manipulation of the digital images 412 acquired from the FIB system 406. For example, the user interface may enable zooming, panning, rotation, of an image output from the FIB system 406

In some embodiments, the image analysis computer 408 may be coupled to an input device 424 (for example, one or more input devices). The input device 424 may include, for example, a keyboard, a mouse, a microphone, or other input devices. In some embodiments, the input device 424 may enable interaction with a user interface displayed on the display 422. For example, in some embodiments, the input device 424 may provide for interaction with a user interface to view and manipulate the digital images 412 acquired from the FIB system 406. In some embodiments, the image analysis computer 408 may output images to other devices, such as a printer.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method of imaging a sample of rock from an oil and gas reservoir, comprising:
   depositing a photoresist on a surface of the rock sample;
   subjecting the photoresist-coated surface of the rock sample to a focused ion beam (FIB) to generate a digital image of the rock sample.

2. The method of claim 1, comprising preparing the rock sample from a core sample obtained from a wellbore extending into the oil and gas reservoir.

3. The method of claim 1, comprising removing the photoresist from the photoresist-coated surface of the rock sample.

4. The method of claim 3, where removing the photoresist comprises exposing the rock sample having the photoresist to an electron beam.

5. The method of claim 1, where the FIB comprises a gallium ion beam.

6. The method of claim 1, where subjecting the photoresist-coated surface of the rock sample to a focused ion beam (FIB) comprises milling a layer of the photoresist-coated surface of the rock sample via the focused ion beam.

7. The method of claim 1, where depositing the photoresist on a surface of the rock sample comprises spin coating the photoresist on the surface of the rock sample.

8. The method of claim 1, where the FIB system comprises a focused ion beam-scanning electron microscopy (FIB-SEM) system.

9. The method of claim 1, where the digital image comprises a two-dimensional (2D) image or a three-dimensional (3D) image.

10. The method of claim 1, where the digital image comprises a three-dimensional (3D) digital image generated from two or more two-dimensional (2D) digital images of the rock sample.

11. The method of claim 1, where the photoresist comprises SU-8 photoresist.

12. The method of claim 1, comprising curing the photoresist at a temperature after depositing the photoresist.

13. A method of analyzing rock from an oil and gas reservoir, comprising:
   obtaining a rock sample having a photoresist deposited on the surface;
   generating a digital image of a rock sample having a photoresist, where the digital image is generating using a focused ion beam (FIB); and
   analyzing the digital image to determine a property of the rock sample.

14. The method of claim 13, where the digital image is a three-dimensional (3D) image, and analyzing the digital image to determine a property of the rock sample comprises analyzing the digital image to determine a porosity of the rock sample.

15. The method of claim 13, comprising depositing a layer of a photoresist on a surface of the rock sample.

16. The method of claim 13, where the photoresist comprises SU-8 photoresist.

* * * * *